US 11,904,877 B1

(12) United States Patent
Chase (10) Patent No.: US 11,904,877 B1
(45) Date of Patent: Feb. 20, 2024

(54) VEHICLE MEDICAL DEVICE INTERFACE SYSTEM

(71) Applicant: Arnold Chase, West Hartford, CT (US)

(72) Inventor: Arnold Chase, West Hartford, CT (US)

( * ) Notice: Subject to any disclaimer, the term of this patent is extended or adjusted under 35 U.S.C. 154(b) by 0 days.

(21) Appl. No.: 17/951,467

(22) Filed: Sep. 23, 2022

(51) Int. Cl.
| | |
|---|---|
| *B60W 50/08* | (2020.01) |
| *B60Q 9/00* | (2006.01) |
| *A61B 5/00* | (2006.01) |
| *H04L 12/40* | (2006.01) |
| *A61B 5/18* | (2006.01) |
| *B60W 40/08* | (2012.01) |

(52) U.S. Cl.
CPC ............ *B60W 50/082* (2013.01); *A61B 5/18* (2013.01); *A61B 5/6893* (2013.01); *A61B 5/742* (2013.01); *B60Q 9/00* (2013.01); *B60W 40/08* (2013.01); *H04L 12/40* (2013.01); *B60W 2040/0872* (2013.01); *B60W 2540/221* (2020.02); *B60W 2720/10* (2013.01); *B60W 2720/24* (2013.01); *H04L 2012/40215* (2013.01)

(58) Field of Classification Search
None
See application file for complete search history.

(56) References Cited

U.S. PATENT DOCUMENTS

| | | | |
|---|---|---|---|
| 8,207,859 B2 * | 6/2012 | Enegren | A61B 5/1112 340/576 |
| 8,344,847 B2 * | 1/2013 | Moberg | A61M 5/16831 600/300 |
| 10,583,842 B1 * | 3/2020 | Gunaratne | G06N 20/00 |
| 11,392,117 B2 * | 7/2022 | Pal | A61B 5/6801 |
| 2019/0391581 A1 * | 12/2019 | Vardaro | A61B 5/02055 |

* cited by examiner

*Primary Examiner* — Todd Melton
(74) *Attorney, Agent, or Firm* — CANTOR COLBURN LLP (57) ABSTRACT

A vehicle and a method of operating a system operably connected to a personal medical device having a sensor is provided. The vehicle includes an indicator device having at least one of an audio device or visual indicator device. A medical device display interface is coupled to communicate with the personal medical device. A controller is operably coupled to the medical device display interface and the indicator device. The controller is operable to receive a first signal from the medical device display interface and activate the indicator device in response to the first signal including data regarding an undesired condition.

30 Claims, 3 Drawing Sheets

VEHICLE MEDICAL DEVICE INTERFACE SYSTEM

BACKGROUND OF THE DISCLOSURE

The subject matter disclosed herein relates to a vehicle monitoring and control system, and in particular to a vehicle interface that cooperates with a medical sensor or device for alerting the operator or controlling the vehicle in the event of an undesired medical event.

Modern vehicles have numerous systems that assist the vehicle operator in the operation of the vehicle. In the case of autonomous vehicles, the control of the vehicle is performed by the vehicle itself with little or no direct action by the operator. For people with severe medical conditions or disabilities, vehicles may be modified to accommodate the vehicle operator's condition. However, these modifications are costly and are typically only performed in certain instances.

For most people who have chronic medical conditions there is no imposition of formal driving restrictions, so inevitably there may be times when persons with such chronic conditions that are actively operating a vehicle may experience an undesired condition, such as low blood sugar, heartbeat irregularities, low blood pressure, or other effects of various medical conditions for example. In many of these instances a vehicle operator may have a medical device(s) present that is already continually monitoring the parameters of such conditions. However, these readings cannot benefit an active vehicle operator for a number of logistical reasons. First, while these devices have the capability of offering continuous visual readouts, due to power considerations the readout displays generally blank after a few seconds of operation to extend the device's operational battery life. Second, even if a medical device display did not blank out, a vehicle operator is typically not operationally and practically able to avail themselves of this data in a timely and continuous manner while actively operating the vehicle.

Most medical devices are bodily, or belt worn, often worn under one or more layers of clothing and/or outer jackets, placed in a purse or other enclosure, etc. This means as a practical matter a vehicle operator is not readily able to see the progression of visual readouts which then inherently precludes a lack of anticipatory responsive action(s) to such conditions such as ingesting carbohydrates (for diabetics) or taking additional medication to correct a developing situation in a timely manner.

Even though body worn continuous monitoring medical devices are constantly updating their relevant information, without a driver actually being able to immediately benefit from such information in real time, the information is of limited value. Presently, without having a direct visualization of a device's display in real-time while operating the vehicle, this often results in a vehicle operator first becoming aware of abnormal medical conditions after such conditions have already progressed to the point of physical impairment and/or the triggering one or more an audible alarm(s). Even if an audible alarm is generated, a person is generally merely alerted to the existence of one or more urgent conditions without the benefit of knowing exactly which condition is generating an alert. Even if a vehicle operator had the display of a medical device already uncovered and nearby, the physical process involved in attempting to see what the display was showing while driving would be cumbersome at best.

Recognizing that most medical devices that are bodily worn typically blank their display screens until they are manually "woken up", as a practical matter for someone that is actively operating a vehicle this means that in order view a device's information readout from a medical device screen several steps need to be taken: First the device needs to be brought into a readable position by physically relocating it. Depending on the location of the medical device such device may need to be physically seized from a belt holster, etc., or if wrist worn moving the arm that holds the device to a position in front of the driver, retracting a shirt sleeve, coat, or other article of clothing to uncover the device, and then activating/waking up the screen display by pushing one or more buttons with a second hand action, and then taking the time to look away from the road to actually see the information. It should be appreciated that any of these actions result in undesired vehicle operating practices. Further, additional effort is likely needed by making further key presses, etc. to acknowledge an alarm and/or take responsive action such as suspending insulin delivery or commanding an insulin pump to bolus additional insulin while operating the vehicle.

Further, as discussed above, while many devices have built-in audible alarms they are inherently limited as to their alarm output volume so given many typical driving conditions these alarms may be easily masked by either being covered by clothing, road noise, a vehicle operator or passenger listening to the vehicle's entertainment system at loud volumes, windows or a convertible top being open, or a combination of these conditions. Further, due to traffic laws in many areas that prohibit the use of any hand-held devices most vehicles are now equipped with built-in "hands-free" capability. Ironically, when drivers are using hands-free systems to make calls (which typically output at high volume levels so as to overcome ambient noise interference), they also may unintentionally mask medical device alarms as well since such hands-free output levels typically operate at sound levels much higher than those of medical device alarms. Finally, the onset of many chronic conditions while driving may result in diminished alertness and awareness on the part of the driver, increasingly so as these conditions get progressively worse causing the chances for an undesired operating event caused by a degradation of the vehicle operator's abilities to increase.

While existing vehicle control systems are suitable for their intended purposes the need for improvement remains, particularly in providing a vehicle medical device interface with the features described herein.

BRIEF DESCRIPTION OF THE DISCLOSURE

According to one aspect of the disclosure, a vehicle having a system operably connected to a personal medical device having a sensor is provided. The vehicle includes an indicator device having at least one of an audio device or visual indicator device. A medical device display interface is coupled to communicate with the personal medical device. A controller is operably coupled to the medical device display interface and the indicator device. The controller is operable to receive a first signal from the medical device display interface and activate the indicator device in response to the first signal including data regarding an undesired condition.

In addition to one or more of the features described herein, or as an alternative, further embodiments of the system may include the activating of the indicator device also causing the activating of at least one of a sound from the audio device or displaying a message on the visual indicator.

In addition to one or more of the features described herein, or as an alternative, further embodiments of the system may include the controller being further operable to control at least one of a speed or a direction of the vehicle in response to the first signal.

In addition to one or more of the features described herein, or as an alternative, further embodiments of the system may include the controller being further operable to dispense a medical agent in response to the first signal.

In addition to one or more of the features described herein, or as an alternative, further embodiments of the system may include the controller being further operable to receive a second signal in response to an action by a vehicle operator.

In addition to one or more of the features described herein, or as an alternative, further embodiments of the system may include the action comprising at least one of speaking a command, activating an actuator, or touching a graphical user interface on the visual indicator.

In addition to one or more of the features described herein, or as an alternative, further embodiments of the system may include the controller being further operable to activate a communications circuit when an action is not performed within a predetermined amount of time.

In addition to one or more of the features described herein, or as an alternative, further embodiments of the system may include the controller being configured to receive a third signal from the communications circuit and controlling the direction and speed of the vehicle to move the vehicle to a medical facility.

In addition to one or more of the features described herein, or as an alternative, further embodiments of the system may include the indicator device, medical device display interface, and controller being connected by a Controller Area Network (CAN) bus.

In addition to one or more of the features described herein, or as an alternative, further embodiments of the system may include the personal medical device being connected to the medical device display interface by one of a Universal Serial Bus (USB) connector, an Onboard Diagnostics (OBD) port, or a wireless connection.

In addition to one or more of the features described herein, or as an alternative, further embodiments of the system may include the first signal being a plurality of first signals that are received on a continuous, periodic, or periodic updated basis.

In addition to one or more of the features described herein, or as an alternative, further embodiments of the system may include the controller being further operable to display the data from the plurality of first signals on the visual indicator when each of the first signals is received.

In addition to one or more of the features described herein, or as an alternative, further embodiments of the system may include the controller being further operable to display data from the plurality of first signals on the visual indicator when a change in the data exceeds a threshold.

In addition to one or more of the features described herein, or as an alternative, further embodiments of the system may include the indicator device being operably coupled to the vehicles infotainment system.

In addition to one or more of the features described herein, or as an alternative, further embodiments of the system may include the audio device comprises speakers integrated into the vehicle.

In addition to one or more of the features described herein, or as an alternative, further embodiments of the system may include the visual indicator comprising a display screen integrated into a dashboard of the vehicle.

In addition to one or more of the features described herein, or as an alternative, further embodiments of the system may include the sensor being positioned on the vehicle operator.

In addition to one or more of the features described herein, or as an alternative, further embodiments of the system may include the sensor comprising a plurality of sensors, at least one of the plurality of sensors being positioned on a person other than the vehicle operator.

In accordance with another aspect of the disclosure, a method of operating a vehicle is provided. The method includes monitoring a medical condition of a vehicle operator with a medical device having a sensor. A first signal is transmitted from the medical device to a medical device display interface, the first signal indicating a medical parameter of the vehicle operator measured by the sensor. A controller monitors the first signal received via the medical device display interface and activates an indicator device in response to the medical parameter crossing a threshold, the indicator device being integral with the vehicle.

In addition to one or more of the features described herein, or as an alternative, further embodiments of the method may include the step of activating the indicator device includes activating at least one of a sound from an audio device or displaying a message on a visual indicator.

In addition to one or more of the features described herein, or as an alternative, further embodiments of the method may include receiving an input signal from the vehicle operator after the indicator device is activated; and dispensing a medical agent with the medical device in response to receiving the input signal.

In addition to one or more of the features described herein, or as an alternative, further embodiments of the method may include the input signal being received via a microphone within the vehicle.

In addition to one or more of the features described herein, or as an alternative, further embodiments of the method may include activating a communications circuit within the vehicle when an input signal is not received from the vehicle operator within a predetermined amount of time after the indicator device is activated.

In addition to one or more of the features described herein, or as an alternative, further embodiments of the method may include receiving, via the communications circuit, a second signal from a medical personnel; and controlling the direction and speed of the vehicle to move the vehicle to a medical facility.

In addition to one or more of the features described herein, or as an alternative, further embodiments of the method may include receiving, at the controller from a vehicle telematic device, a position of the vehicle; and wherein the activating of the communications circuit includes transmitting the position of the vehicle.

In addition to one or more of the features described herein, or as an alternative, further embodiments of the method may include causing the vehicle to perform one of a change in speed and a change in direction when an input signal is not received within a predetermined amount of time after the indicator device is activated.

In addition to one or more of the features described herein, or as an alternative, further embodiments of the method may include the activating of the indicator device is performed when a rate of change of the medical parameter crosses the threshold.

In addition to one or more of the features described herein, or as an alternative, further embodiments of the method may include the activating of the indicator device is performed when a difference of the parameter between a first time and a second time crosses a second threshold.

In addition to one or more of the features described herein, or as an alternative, further embodiments of the method may include the first signal is transmitted on a periodic, aperiodic, or continuous basis.

These and other advantages and features will become more apparent from the following description taken in conjunction with the drawings.

BRIEF DESCRIPTION OF DRAWINGS

The subject matter, which is regarded as the disclosure, is particularly pointed out and distinctly claimed in the claims at the conclusion of the specification. The foregoing and other features, and advantages of the disclosure are apparent from the following detailed description taken in conjunction with the accompanying drawings in which:

The detailed description explains embodiments of the disclosure, together with advantages and features, by way of example with reference to the drawings.

DETAILED DESCRIPTION OF THE INVENTION

The present disclosure, a Vehicle Medical Device Display Interface (VMDDI) provides for an interface and integration between medical devices, regardless of their location within a vehicle, and the audio and visual data delivery to a vehicle's operator. In some embodiments, by utilizing either a dedicated stand-alone display(s) or those display devices that are already built into the vehicle, this allows real-time (or near real-time) continuous medical conditions to not only be readily presented, but also continuously monitored by a vehicle operator in a safe and timely fashion. This results in a heightened awareness of any monitored medical abnormalities before such conditions worsen and potentially cause a vehicle to lose control of their vehicle.

In an embodiment, VMDDI allows a driven vehicle itself to take on the role of actively monitoring and responding to the health and condition of its operator in addition to the vehicle's "usual" mechanical parameter monitoring (oil pressure, tire pressure, etc.), thus potentially leading the way for the vehicle itself to take responsive operator-directed medical related action(s) as well.

In an embodiment, the VMDDI monitors an operator's medical condition and also allows a vehicle operator to take responsive medical device action(s) using controls located on a vehicle's steering wheel, dashboard, and/or by voice response commands (e.g. using the vehicles voice-activated control system). Further, in other embodiments VMDDI may also allow for automatic responses/actions to take place on the part of a vehicle if, for instance, no responsive acknowledgments or actions on the part of the vehicle operator were taken in response in the context of an occupied operator's seat with no vehicle motion for a period of time. In these embodiments, the VMDDI may automatically and responsively take an action, such as suspend or increase the infusion of medical agents (i.e. insulin) for example, as well as report the driver's medical condition to first-responder personnel or telematics companies for medical personnel dispatch in the event of a crash or determined driver unconsciousness. Further, in still other embodiments the VMDDI may be incorporated into Autonomous Vehicles (AV's) which in addition to reporting such medical conditions, the AV may also be remotely commanded by medical or other personnel to drive to a medical facility rather than waiting for a response by emergency first-responder personnel.

It should be noted that for the purpose of clarifying terms used herein, the term "continuous" monitoring may be taken to mean a regular continuous series of sequential periodic readings or signals. Further, in some embodiments, the monitoring may be performed on a continuous periodic or an aperiodic basis to generate a plurality of signals.

With recent government regulation (e.g. the US Food & Drug Administration and other agencies) mandating that proprietary protocols for medical devices transition from proprietary to "open" operative standards, this now allows medical device link interoperability at a level not seen before thus enabling not only medical data transfer between devices but also allowing actual operative control between devices.

With such increasingly open standards for medical data access capability, in some embodiments this allows VMDDI to either directly access specific medical data from medical sensing devices to allow, for example, accessing a driver's blood glucose level directly from an active glucose sensor and/or via interconnected insulin pumps, etc. thus allowing VMDDI to monitor either the "raw" sensor data (directly from a sensor) or from a medical device that has already collected and "processed" and analyzed such data to allow a more focused level of data and/or alarms.

The operative connection between medical devices and VMDDI may take several forms, through either wired or wireless communication mediums, and within each type of communication medium, there may be further multiple embodiment pathways. In the case of a "wired" connection a simple USB to USB cable would be used between a medical device(s) and a USB jack that may already reside within a vehicle. Such a data connection would allow the medical device to output data directly to an interface with the vehicle's USB hub which is operatively connected to a vehicle's Controller Area Network (CAN bus). Other types of wired connections may include connecting to an Onboard Diagnostics (ODB) port).

In some embodiments, the VMDDI would also be operatively equipped with wireless bi-directional capabilities that are in common use such as Bluetooth™ZigBee™, or other protocols. In some embodiments, such wireless connectivity may take the form of a dedicated VMDDI wireless adapter connected to a vehicle's USB or OBD ports, or by utilizing existing wireless connectivity that may already exist in a vehicle and is operatively connected to a vehicle's CAN bus.

This communications connectivity not only allows real-time medical condition updates from a medical device to utilize existing systems and features of a vehicle, such as the vehicle's audio amplifier(s) and sound system for aural audio alerting for example, but also to utilize the windshield as a display device either through a "head-up" display or by using embedded active display elements (such as transparent OLED's) in a dedicated part of the windshield, the existing dashboard display(s) of a vehicle, or by using a separate dedicated "stand-alone" visual display capable of real-time presentation of changing medical conditions, whether they are routine and/or urgent in nature for example. Alternatively, controls such as pushbuttons (either discrete-physical or touchscreen) may be also incorporated into the stand-alone display to acknowledge information with a single hand for example.

As pending urgent medical conditions are of the highest priority to a vehicle operator, in an undesired medical data situation VMDDI would take priority over any lower priority audio and/or visual data that was being displayed or presented. As an example, information such as entertainment-related material would be replaced by VMDDI on a priority basis by a device's medical information output during the pendency of an undesired medical condition or event for a relevant period of time. In an embodiment, the modality used to communicate the medical condition updates may be based on a severity level or urgency level of the medical condition. In still further embodiments, the intensity level of the modality used may dynamically change, effecting parameters such as the alert sound level, the color or the brightness of the communicated information, etc.

In the case of a direct operative connection with a medical sensor, appropriate alarm triggering parameters would be defined into VMDDI, along with the desired device(s) serial numbers, user identifying information, and other information to allow VMDDI to monitor desired specific sensor(s) or devices. Advantageously, one VMDDI embodiment, even without an operative data communications link having been established between VMDDI and a medical system within the vehicle, the VMDDI may utilize components within the vehicle to acquire sounds, such as a particular alarm sound, vibration sound and pattern(s), audio frequency(s), or specific cadences indicative of a specific alarm for example. Further, the system may be configured or "trained" to identify specific audible signature(s) in the acquired sound data and subsequently allow VMDDI to trigger a predetermined response, either audibly and or visually upon determining the identified sound has the audible frequency, cadence, or other audible characteristic.

In an embodiment, VMDDI may report medical information to a driver in one of four operational display modes. First, the VMDDI may be off, meaning no display or audio alarms are presented. Second, the VMDDI may be operated in a continuous mode, meaning a continuous display of data is provided to the vehicle operator and dynamically updated in a timely fashion. Third, the VMDDI may operate in a mode that monitors for a defined change in medical condition. Fourth, the VMDDI may operate in an alarm-only mode. In other embodiments, additional modes may be provided that in addition to visual displays, other indicators such as audio warnings and updates (e.g. the system provides an audio message of "low blood sugar") may also be used to alert the vehicle operator.

In the third mode, that monitors for a change in medical condition, data is displayed only during significant changes in a medical condition, e.g., if one or more of the monitored medical parameters indicate to VMDDI high, low, or otherwise undesired threshold data readings. In this mode, in addition to any empirical parameter readings that may be displayed, additional informative graphics, for instance, in the form of upward, downward, or other directional arrows may be also displayed for example. These arrows may be further modified by displaying different arrow lengths, simultaneous number of arrows, etc. to further indicate the trend or rate of condition changes, as well as incorporating the graphics with different display colors (e.g. "red"for rapidly changing conditions) as well as "flashing" the displayed information to further define the urgency of a pending medical condition in order to better attract the drivers attention in the event of urgent medical situations.

In the fourth mode, the VMDDI operates to indicate an alarm condition. In this mode visual as well as aural alarms indicating an urgent medical condition, such as abnormal heart rate situations for example, are indicated. Such "overall" information may alternate with other informational modes if appropriate.

As discussed herein, the bi-directional connectivity between VMDDI, medical device(s), vehicle dashboard (e.g. infotainment system), and/or vehicle interactive voice commands may be employed to wake up, acknowledge, or allow actions by the medical devices to be taken (such as suspending insulin delivery) in response to an input or command from the vehicle operator.

If a medical condition(s) fit within a preset criteria such as detecting heart rhythms indicative of a heart attack, VMDDI through the CAN bus would notify telematic systems installed in the vehicle and/or other in-vehicle systems of the medical event in a manner similar to the automatic crash alert functionality provided in prior art vehicles. In the case of VMDDI, in addition to the telematics system reporting a vehicle's location, medical information such as low/high driver "blood sugar" or heart rhythm abnormalities, for example, may also be transmitted to the telematics operator for use and relaying to arriving medical responders.

In an embodiment, with medical conditions where VMDDI senses an overt undesired situation, e.g., a situation that may result in an immediate impairment to a driver's ability to control a vehicle (i.e. a driver becoming unconscious), in vehicles that are equipped with driving assist systems (as well as autonomous vehicles) the system may optionally reduce speed and/or change the direction of the vehicle to bring the vehicle to a desired location (e.g. the shoulder of the road). The driving assist system may also slow and then stop the vehicle, engage the emergency flashers, unlock the doors, or a combination of the foregoing for example. Such actions may also be relayed to telematics operators along with the stopped vehicle's location.

In embodiments where vehicles that are equipped with advanced driving assist capability that are below full autonomy capability, such driving-assist systems may be continuously checking to make sure the driver is paying sufficient attention to the road (e.g. actively viewing ambient roadway conditions and locations of other vehicles) before shutting down the assist system for non-compliance. In some embodiments where there is a severe medical impairment while operating under driving assist systems, it is desired for the driver to focus on monitoring and responding to their developing medical condition which may result in exceeding the preset "driver attention" grace period or time threshold of an assist system while it is most desired. In such embodiments, the VMDDI through the CAN bus may indicate to the vehicle the pending undesired medical condition which would allow the driving assist feature to provide an extended amount of active assist time before shutting down the driver assist system while under an active medical alarm.

With ongoing medical agency approvals that allow younger and younger patients to use worn medical devices, it should be appreciated that VMDDI has the capability to monitor and display to a vehicle operator the medical parameters from persons other than a vehicle's operator itself. With various VMDDI embodiments passenger(s) such as infants, children, or adults that may be in a back seat and are wearing (or have implanted) medical devices to also be operatively connected to VMDDI so as to let the vehicle operator have a safe and ongoing real-time heightened medical situation awareness of the vehicle's medically monitored occupants. This is an improvement over the present method wherein a vehicle operator must stop the vehicle and manually check a medical device(s) on one or more passengers, especially in the case of passengers that are seated in rear seating areas being continuously monitored rather than only benefitting from a "snapshot" medical ascertainment. It should further be appreciated that VMDDI is capable of simultaneously monitoring multiple vehicle occupants as long as each person desires to be monitored and registers their devices with VMDDI.

Figure 1:
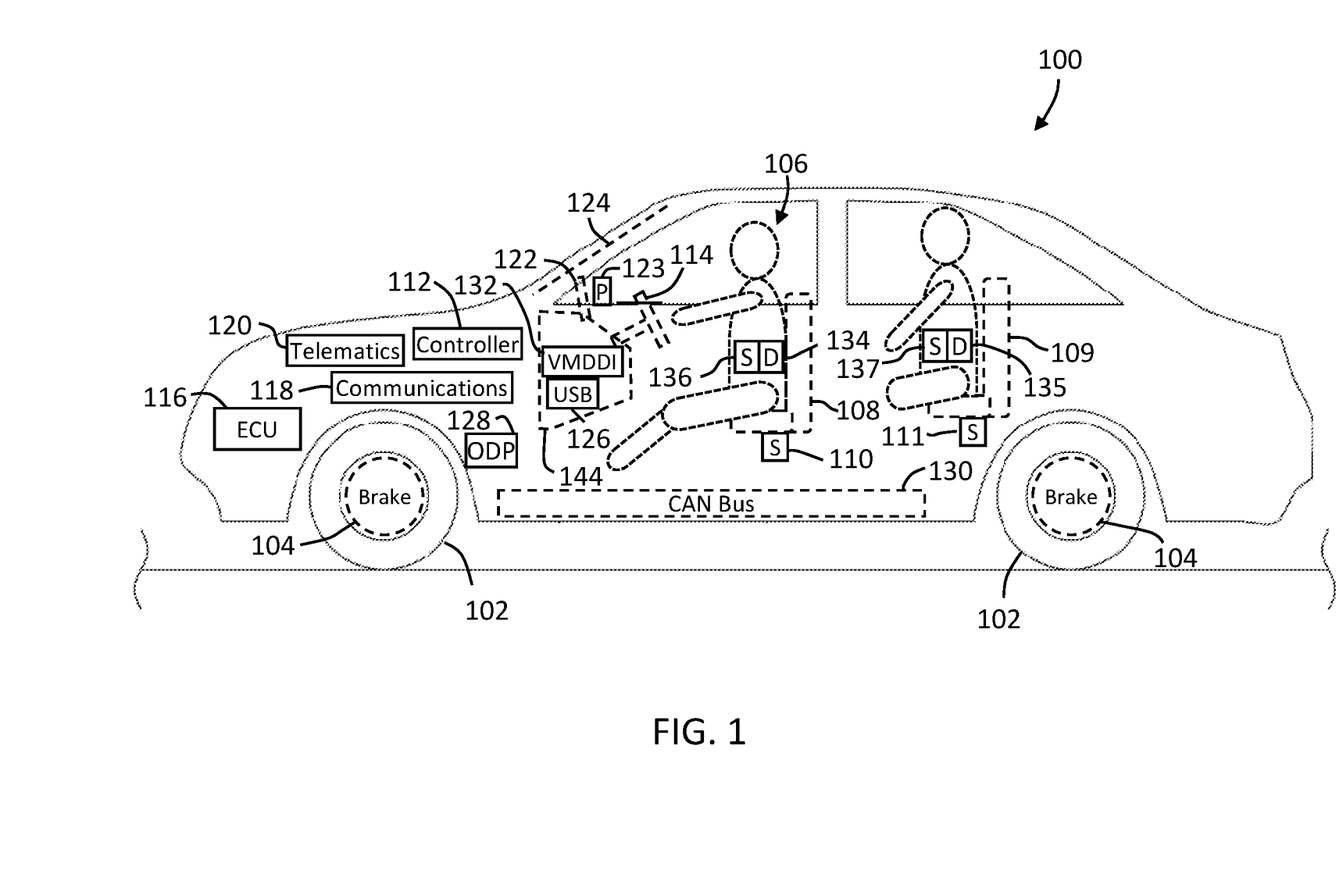
FIG. 1 shows an exemplary side view of a vehicle having a medical device display interface in accordance with an embodiment.

Referring now to FIG. 1, an embodiment is shown of a vehicle 100. The vehicle 100 may be an automobile for example, having a plurality of wheels 102 that allow the vehicle 100 to roll under energy provided by an engine or motor for example. Each of the wheels may have a brake system 104 that allows the vehicle to be slowed or brought to a stop, such as when the vehicle operator 106 presses on a brake pedal or if a driver assist system identifies the vehicles speed should be decreased. The vehicle 100 includes one or more seats 108. As discussed herein, the seat 108 may include one or more sensors 110 that allow one or more vehicle control systems 112 to determine whether the vehicle operator is seated in the seat 108. In some embodiments, there may be additional sensors 111, such as operably coupled with passenger seats 109. In some embodiments, the sensor 110 may further provide data to the control systems 112 on whether the operator has moved (e.g. shifted position). In some embodiments, the vehicle 100 may include control devices, such as a steering wheel 114, brake and accelerator pedals and a transmission or "gear shift" mechanism that allow vehicle operator 106 to control/operate the vehicle.

The vehicle 100 may include a variety of subsystems that assist in operating the vehicle. These systems may include an engine control unit 116, a communications circuit 118, a telematics system 120, an infotainment system, an audio system, a video display system 122 and the like. It should be appreciated that the video display system 122 may be integrated into the vehicle instrument panel or the vehicle infotainment system. In an embodiment, the vehicle 100 may include a windshield 124 that includes a means for displaying information (e.g. a heads up display or embedded active display elements (e.g. transparent OLED's e.g. "TOLED"). The vehicle may further include ports or communications connections, such as a Universal Serial Bus (USB) 126, an onboard diagnostics port (ODP) 128, WiFi, and/or Bluetooth™ connections. In an embodiment, the vehicle 100 may include a CAN bus 130 that allows the different subsystems, sensors, and devices (e.g. microphones, speakers) to communicate with the control system 112. It should be appreciated that while FIG. 1 shows a single block for controller 112, this is for example purposes and the claims should not be so limited. The functionality of control system 112 or controller described herein may be distributed between multiple computing devices. In some embodiments, the control system 112 may be connected to a distributed computing network or "cloud" based computer network.

As discussed herein, the vehicle 100 further includes a VMDDI module 132. It should be appreciated that while the VMDDI module 132 is illustrated as a discrete component, this is for example purposes and the functionality of the VMDDI module 132 may be incorporated into another subsystem, such as the controller 112 or an infotainment system for example. In an embodiment, the ports and communications connections, such as the USB port 126 for example, are connected to the VMDDI module 132 via the CAN bus 130. In some embodiments, the VMDDI module 132 is added to the vehicle by coupling the module to one of the ports 126, 128 or via a wireless connection (e.g. WiFi or Bluetooth).

In an embodiment, the vehicle operator 106, has a wearable medical device 134 having one or more medical sensors 136 that measure parameters associated with a medical condition, such as but not limited to blood sugar levels, blood pressure, heart rate for example. The medical device 134 may further include one or more systems that dispense a medical agent to the vehicle operator 106. As used herein a medical agent may be a substance, such as insulin for example, that may regulate or alleviate the monitored medical condition. As discussed herein, the medical device 134 is coupled to communicate with the VMDDI module 132, and/or medical sensors 136. In an embodiment, the medical device 134 establishes the communication connection with the VMDDI module 132 when the vehicle is started or when the vehicle operator 106 enters the vehicle 100.

In an embodiment, the VMDDI module 132 may be operably connected to other medical devices and sensors, such as medical device 135 and sensor 137 on a passenger in a rear seat 109 for example. It should be appreciated that the VMDDI module 132 may be configured to monitor sensor and device data from multiple persons in the vehicle 100 and provide individualized display and alert signals to the vehicle operator. This provides advantages in allowing the vehicle operator to monitor the conditions of passengers on a continuous, periodic or aperiodic basis.

Figure 2:
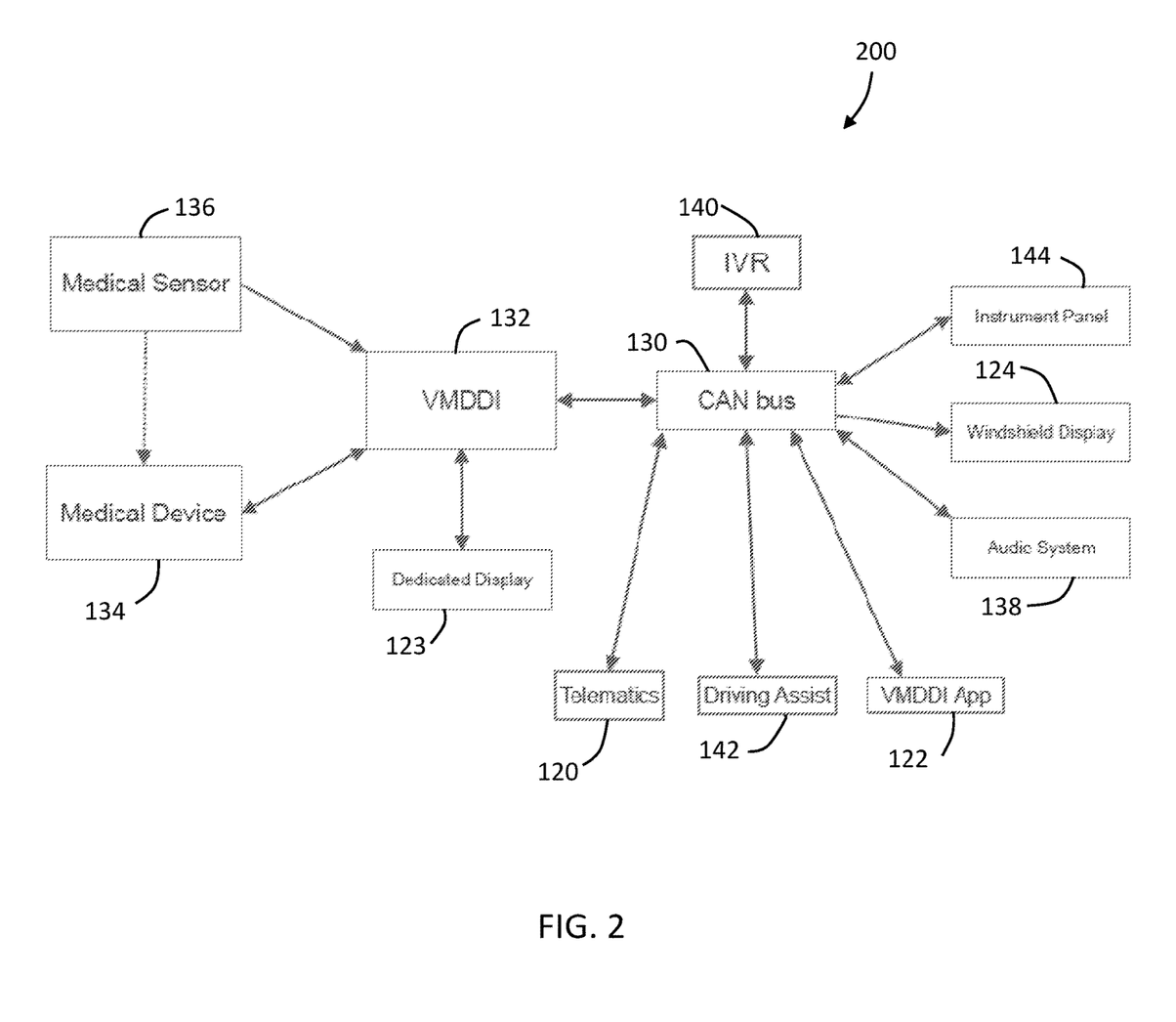
FIG. 2 shows an exemplary data flow diagram for the medical device display interface of FIG. 1.

Referring now to FIG. 2, data flow 200 is shown from the medical device 134 through the VMDDI module 132 to the subsystems of vehicle 100. In this embodiment, the medical device 134 receives data from a medical sensor 136. In an embodiment, the medical sensor 136 is directly coupled to the VMDDI module 132. The medical sensors 136 data is transmitted to the VMDDI module 132. In an embodiment, the dedicated display 123 may be a touchscreen Under normal operation (i.e. no undesired medical condition), and depending on the mode of operation (e.g. continuous, change in condition, or alarm), the VMDDI module 132 may in turn transmit a signal with the data to a dedicated display 123 or via the CAN bus 130 to another indicator device, such as the instrument panel 122, a windshield 124 display or an audio system 138.

Further, the VMDDI module 132 may also receive signals such as when the vehicle operator acknowledges an alert on the dedicated display 123. The VMDDI module 132 may further receive signals with data from the CAN bus 130, such as from an interactive voice response unit 140 that receives audio input from the vehicle operator, such as via a microphone integrated into the interior of the vehicle 100. Inputs may also come from the instrument panel 144, the telematics system 120, a driver assist system 142 or an software application on the infotainment system 122.

Figure 3:
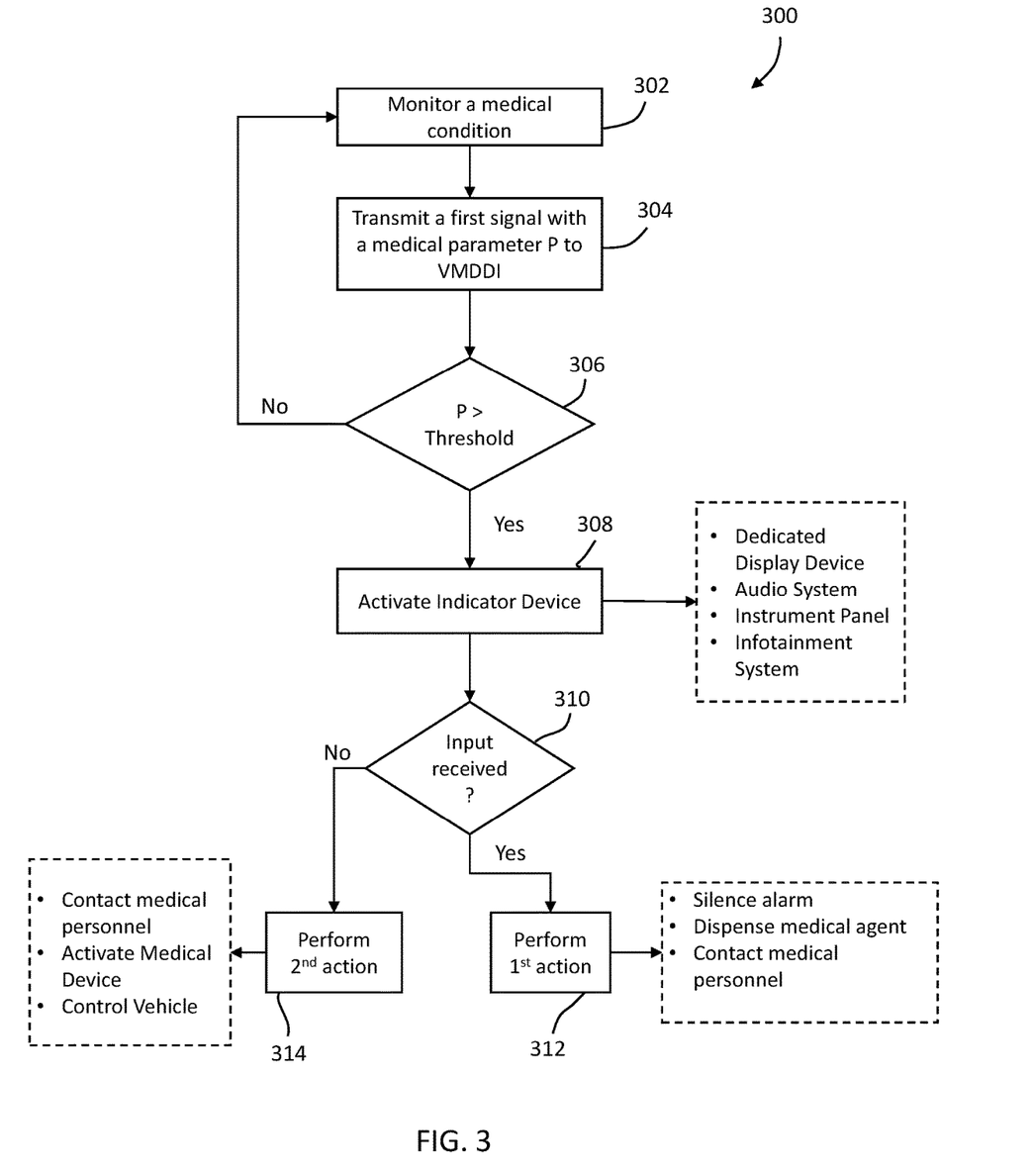
FIG. 3 shows an exemplary flow diagram of a method of operating the medical device display interface of FIG. 1.

Referring now to FIG. 3, an embodiment is shown of a method 300 of operating the vehicle 100 and the VMDDI module 132. The method 300 begins in block 302 where the medical condition is monitored, such as with medical sensors 136 and/or medical device 134 for example. The method 300 then proceeds to block 304 where a signal indicating the medical parameter is transmitted to the VMDDI module 132. The VMDDI module 132 then evaluates in query block 306 that the parameter and determines if one or more thresholds have been crossed. For example, if blood sugar is being monitored the VMDDI module 132 determines whether the parameter goes above a predetermined threshold or below a predetermined threshold. If the threshold(s) is not crossed, then the method 300 loops back to block 302 and continues to measure the parameter.

When the parameter is at a level where the threshold(s) is crossed the method 300 proceeds to block 308 where an indicator device is activated. The indicator device may include the dedicated display 123, the infotainment system 122, the instrument panel 144, the windshield 124 display, and audio system 138. The method 300 then proceeds to query block 310 where the VMDDI module 132 waits a predetermined amount of time to see if an input received. The input may be an audible input, such as through an interactive voice response unit 140 or a touchscreen on the dedicated display 123 or instrument panel 144 for example. When the query block 310 returns a positive, meaning the vehicle operator provided an acknowledge input, such as through the interactive voice response unit 140 for example, the method 300 proceeds to block 312 where a first type of action is performed. The first type action may depend on the input received from the vehicle operator. For example, if the vehicle operator wants to acknowledge the alert, but take no action, the VMDDI module 132 may silence the alarm for a predetermined amount of time. The vehicle operator may also commend other actions, such as dispensing a medical agent, contacting specific medical personnel (e.g. the operators personal doctor), contacting emergency medical responders, or contacting a predetermined contact (e.g. their spouse or partner) for example.

When the query block 310 returns a negative, meaning there was no response from the vehicle operator, the method 300 proceeds to block 314 where a second type action is performed. In some embodiments, the second type action, the VMDDI module 132 may take more proactive steps to prevent and undesired event from occurring in the event the vehicle operator is impaired by a medical condition. In an embodiment, the method 300 may use additional information sensors in the vehicle 100, such as the seat sensor 110 or sensors that detect movement of the steering wheel. Depending on the measurements by these systems, the VMDDI module 132 may take different actions. In an embodiment, where the sensors indicate movement, such as the operator actively moving the steering wheel or moving in a seat, the VMDDI module 132 may wait a predetermined amount of time (e.g. depending on the urgency level of the medical condition) and activate the indicator device (block 308) a second time before taking further steps.

In an embodiment, where the medical condition indicates an urgency level that is high, meaning there is a probability above a threshold that the vehicle operator's driving function may be impaired due to the medical condition, the VMDDI module 132 may perform one or more actions to avoid an undesired event from occurring with the vehicle or to transport the vehicle operator to a medical facility for further evaluation. In an embodiment, the second type action in block 314 may include performing multiple steps, including contacting emergency personnel, changing the speed and/or direction of the vehicle, or activating a response by one or more medical devices. In an embodiment, the second type action may include activating a driver assist system 142 in the vehicle 100 to move the vehicle 100 to a shoulder or side of the roadway and turning on the vehicles hazard lights while simultaneously contacting emergency medical or first-responder services. In another embodiment, where the vehicle 100 includes autonomous driving capabilities, the VMDDI module 132 may include identifying the closest medical facility (e.g. a hospital) and controlling the speed and direction of the vehicle 100 to transport the vehicle operator to the medical facility.

It should be appreciated that while embodiments herein may refer to particular medical conditions, such as diabetes or a heart condition for example, this is for example purposes and the claims should not be so limited. In other embodiments, other medical devices, sensors and medical conditions may be monitored and actions appropriate for those medical conditions taken. For example, medical conditions may include, but are not limited to vertigo, cerebrovascular disease, strokes, transient ischaemic attack (TIA), multiple sclerosis, Parkinson's disease, motor-neuron disease, aneurysms, fainting/blackouts, lung-diseases/oxygen-use, high or low blood pressure, angina, irregular heart-beat, seizures, and epilepsy for example.

It should be appreciated that while the term vehicle may be used herein in the context of an "automotive" vehicle, this is for example purposes and the claims should not be so limited. As used herein, the term "vehicle" may be any transportation system, such as but not limited to automobiles, motorcycles, trucks, vans, buses, construction equipment, trains, planes, and boats for example.

The term "about" is intended to include the degree of error associated with measurement of the particular quantity based upon the equipment available at the time of filing the application. For example, "about" can include a range of ±8% or 5%, or 2% of a given value.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection." It should also be noted that the terms "first", "second", "third", "upper", "lower", and the like may be used herein to modify various elements. These modifiers do not imply a spatial, sequential, or hierarchical order to the modified elements unless specifically stated.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof While the disclosure is provided in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that the exemplary embodiment(s) may include only some of the described exemplary aspects. Accordingly, the disclosure is not to be seen as limited by the foregoing description, but is only limited by the scope of the appended claims.

What is claimed is:

1. A vehicle having a system operably connectable to a plurality of personal medical devices associated with different medical conditions, each of the plurality of personal medical devices having a sensor, the vehicle comprising:
an indicator device having at least one of an audio device or visual indicator device;
a medical device display interface coupled to bidirectionally communicate with at least one of the plurality of personal medical devices; and
a controller operably coupled to the medical device display interface and the indicator device, the controller being operable to receive a first signal from the medical device display interface and activate the indicator device in response to the first signal including data regarding an undesired condition,
wherein the medical device display interface is configured to be coupled to a Universal Serial Bus (USB) port of the vehicle, an Onboard Diagnostics (OBD) port of the vehicle, or a wireless connection of the vehicle.

2. The vehicle of claim 1, wherein the activating of the indicator device includes activating at least one of a sound from the audio device or displaying a message on the visual indicator.

3. The vehicle of claim 1, wherein the controller is further operable to control at least one of a speed or a direction of the vehicle in response to the first signal.

4. The vehicle of claim 1, wherein the controller is further operable to dispense a medical agent in response to the first signal.

5. The vehicle of claim 1, wherein the controller is further operable to receive a second signal in response to an action by a vehicle occupant.

6. The vehicle of claim 5, wherein the action includes at least one of speaking a command, activating an actuator, or touching a graphical user interface on the visual indicator.

7. The vehicle of claim 5, wherein the controller is further operable to activate a communications circuit when the action is not performed within a predetermined amount of time.

8. The vehicle of claim 7, wherein the controller is configured to receive a third signal from the communications circuit and controlling a direction and a speed of the vehicle to move the vehicle to a medical facility.

9. The vehicle of claim 1, wherein the indicator device, the medical device display interface, and the controller are connected by a Controller Area Network (CAN) bus.

10. The vehicle of claim 1, wherein each of the plurality of personal medical device is connectable to the medical device display interface by one of a Universal Serial Bus (USB) connector, an Onboard Diagnostics (OBD) port, or a wireless connection.

11. The vehicle of claim 1, wherein the first signal includes a plurality of first signals that are received on a continuous, periodic, or periodic updated basis.

12. The vehicle of claim 11, wherein the controller is further operable to display the data from the plurality of first signals on the visual indicator when each of the plurality of first signals is received.

13. The vehicle of claim 11 wherein the controller is further operable to display the data from the plurality of first signals on the visual indicator when a change in the data exceeds a threshold.

14. The vehicle of claim 1, wherein the indicator device is operably coupled to a vehicle infotainment system.

15. The vehicle of claim 14, wherein the audio device includes speakers integrated into the vehicle.

16. The vehicle of claim 15, wherein the visual indicator includes a display screen integrated into a dashboard of the vehicle.

17. The vehicle of claim 1, wherein the sensor is positioned on a vehicle occupant.

18. The vehicle of claim 17, wherein the sensor includes a plurality of sensors, at least one of the plurality of sensors being positioned on a person other than the vehicle operator.

19. A method of operating a vehicle comprising:
providing a medical device display interface bidirectionally connectable to a plurality of personal medical devices associated with a plurality of medical conditions, respectively, the plurality of medical conditions being different;
monitoring one of the plurality of medical conditions of a vehicle occupant with a selected personal medical device of the plurality of personal medical devices, the selected personal medical device having a sensor;
transmitting a first signal from the selected personal medical device to the medical device display interface, the first signal indicating a medical parameter of the vehicle occupant measured by the sensor; and
monitoring, with a controller, the first signal received via the selected personal medical device display interface and activating an indicator device in response to the medical parameter crossing a threshold, the indicator device being integral with the vehicle,
wherein providing a medical device display interface comprises coupling the medical device display interface to a Universal Serial Bus (USB) port of the vehicle, an Onboard Diagnostics (OBD) port of the vehicle, or a wireless connection of the vehicle.

20. The method of claim 19, wherein the activating the indicator device includes activating at least one of a sound from an audio device or displaying a message on a visual indicator.

21. The method of claim 19, further comprising:
receiving an input signal from the vehicle occupant after the indicator device is activated; and
dispensing a medical agent with the medical device in response to receiving the input signal.

22. The method of claim 21, wherein the input signal is received via a microphone within the vehicle.

23. The method of claim 19, further comprising activating a communications circuit within the vehicle when an input signal is not received from the vehicle occupant within a predetermined amount of time after the indicator device is activated.

24. The method of claim 23, further comprising:
receiving, via the communications circuit, a second signal from a medical personnel; and
controlling a direction and a speed of the vehicle to move the vehicle to a medical facility.

25. The method of claim 19, further comprising:
receiving, at the controller from a vehicle telematic device, a position of the vehicle; and
wherein the activating of a communications circuit includes transmitting the position of the vehicle.

26. The method of claim 19, further comprising causing the vehicle to perform one of a change in speed and a change in direction when an input signal is not received within a predetermined amount of time after the indicator device is activated.

27. The method of claim 19, wherein the activating of the indicator device is performed when a rate of change of the medical parameter crosses the threshold.

28. The method of claim 19, wherein the activating of the indicator device is performed when a difference of the medical parameter between a first time and a second time crosses a second threshold.

29. The method of claim 19, wherein the first signal is transmitted on a periodic, aperiodic, or continuous basis.

30. A vehicle having a system operably connected to a personal medical device integral with a vehicle occupant and having a sensor, the vehicle comprising:
- an indicator device having at least one of an audio device or visual indicator device;
- a medical device display interface coupled to bidirectionally communicate with the personal medical device; and
- a controller operably coupled to the medical device display interface and the indicator device, the controller being operable to receive a first signal from the medical device display interface and activate the indicator device in response to the first signal including data regarding an undesired condition;
- wherein the vehicle occupant is not the vehicle operator, and
- wherein the medical device display interface is configured to be coupled to a Universal Serial Bus (USB) port of the vehicle, an Onboard Diagnostics (OBD) port of the vehicle, or wireless connection of the vehicle.

* * * * *